(12) United States Patent
Xu (10) Patent No.: US 8,122,761 B2
(45) Date of Patent: Feb. 28, 2012

(54) BIOSENSOR BASED ON POLYMER CANTILEVERS

(75) Inventor: Yong Xu, Troy, MI (US)

(73) Assignee: Wayne State University, Detroit, MI (US)

( * ) Notice: Subject to any disclaimer, the term of this patent is extended or adjusted under 35 U.S.C. 154(b) by 692 days.

(21) Appl. No.: 11/814,867

(22) PCT Filed: Jan. 20, 2006

(86) PCT No.: PCT/US2006/001870
§ 371 (c)(1),
(2), (4) Date: Jul. 26, 2007

(87) PCT Pub. No.: WO2006/083566
PCT Pub. Date: Aug. 10, 2006

(65) Prior Publication Data
US 2010/0037682 A1    Feb. 18, 2010

Related U.S. Application Data (60) Provisional application No. 60/648,173, filed on Jan. 28, 2005.

(51) Int. Cl.
*G01B 5/28* (2006.01)
(52) U.S. Cl. ............... 73/105; 116/275; 850/30; 850/55; 850/35; 850/37; 850/38; 850/41; 850/52

(58) Field of Classification Search ................. 73/24.01, 73/24.06, 31.01, 31.02, 31.03, 31.05, 61.49, 73/61.75, 61.79, 105; 116/275
See application file for complete search history.

(56) References Cited

U.S. PATENT DOCUMENTS 5,506,829 A * 4/1996 Yagi et al. .................... 369/126
(Continued)

OTHER PUBLICATIONS

Hwang et al., "In-situ quantitative analysis of a prostate-specific antigen (PSA) using a nanomechanical PZT cantilever", First published as an Advance Article on the web Nov. 10, 2004.*

(Continued)

*Primary Examiner* — Hezron E Williams
*Assistant Examiner* — Rodney T Frank
(74) *Attorney, Agent, or Firm* — Brooks Kushman P.C.

(57) ABSTRACT

A microcantilever sensor includes a supporting substrate, a cantilever spring element at least partially disposed over the support substrate, a probe layer disposed over the first side of the cantilever spring element, and a piezoresistive transducer attached to the second side of the cantilever spring element. The cantilever spring element is characterized by having a first side and a second side and comprising a polymer having a Young's modulus less than about 100 Gpa. Sensing systems that incorporate the cantilever sensor of the invention include a detector in communication with the piezoresistive transducer to provide measurements of surface strain changes in the piezoresistive transducer.

20 Claims, 8 Drawing Sheets

U.S. PATENT DOCUMENTS

| | | | |
|---|---|---|---|
| 5,631,463 A * | 5/1997 | Kawasaki et al. | 850/59 |
| 5,719,324 A | 2/1998 | Thundat et al. | |
| 6,475,639 B2 | 11/2002 | Shahinpoor et al. | |
| 6,523,392 B2 | 2/2003 | Porter et al. | |
| 6,575,020 B1 | 6/2003 | De Charmoy et al. | |
| 6,647,766 B2 | 11/2003 | Despont et al. | |
| 6,823,717 B2 | 11/2004 | Porter et al. | |
| 7,073,938 B2 * | 7/2006 | Gianchandani et al. | 374/185 |

OTHER PUBLICATIONS

Chen et al., "Two-Dimensional Micromachined Flow Sensor Array for Fluid Mechanics Studies", Journal of Aerospace Engineering © ASCE / Apr. 2003.*

Pechmann, R. et al., "The Novolever: A new cantilever for scanning force microscopy microfabricated from polymeric materials," Rev. Sci. Instrum. 65 (12), Dec. 1994, pp. 3702-3706.

Thaysen, J. et al., "Polymer-Based Stress Sensor with Integrated Readout," J. Phys. D: Appl. Phys, 35 (2002) pp. 2698-2703.

Guanghua, Wu et al., "Bioassay of prostate-specific antigen (PSA) using microcantilevers," Nature Biotechnology, v. 19, Sep. 2001, pp. 856-860.

Guanghua, Wu et al., "Origin of nanomechanical cantilever motion generated from biomolecular interactions," PNAS, Feb. 13, 2001, v. 98, n. 4, pp. 1560-1564.

* cited by examiner

BIOSENSOR BASED ON POLYMER CANTILEVERS

CROSS-REFERENCE TO RELATED APPLICATIONS

This application claims the benefit of U.S. provisional application Ser. No. 60/648,173 filed Jan. 28, 2005.

BACKGROUND OF THE INVENTION

1. Field of the Invention

The present invention relates to polymer cantilevers that are useful in biosensor applications, and in particular to parylene cantilevers that are useful in such applications.

2. Background Art

Biosensors play a crucial role in disease diagnosis, drug discovery, environment monitoring, prevention of bio-terrorism, and the like. The biosensor usually consists of two parts: a molecular recognition element (receptor coating) and a transducer that converts the recognition event into different physical signals. Various transduction methods, based on thermal, mass, electrochemical and optical phenomena occurring during the biomolecular recognition event, have been implemented for biological sensing.

Figure 1:
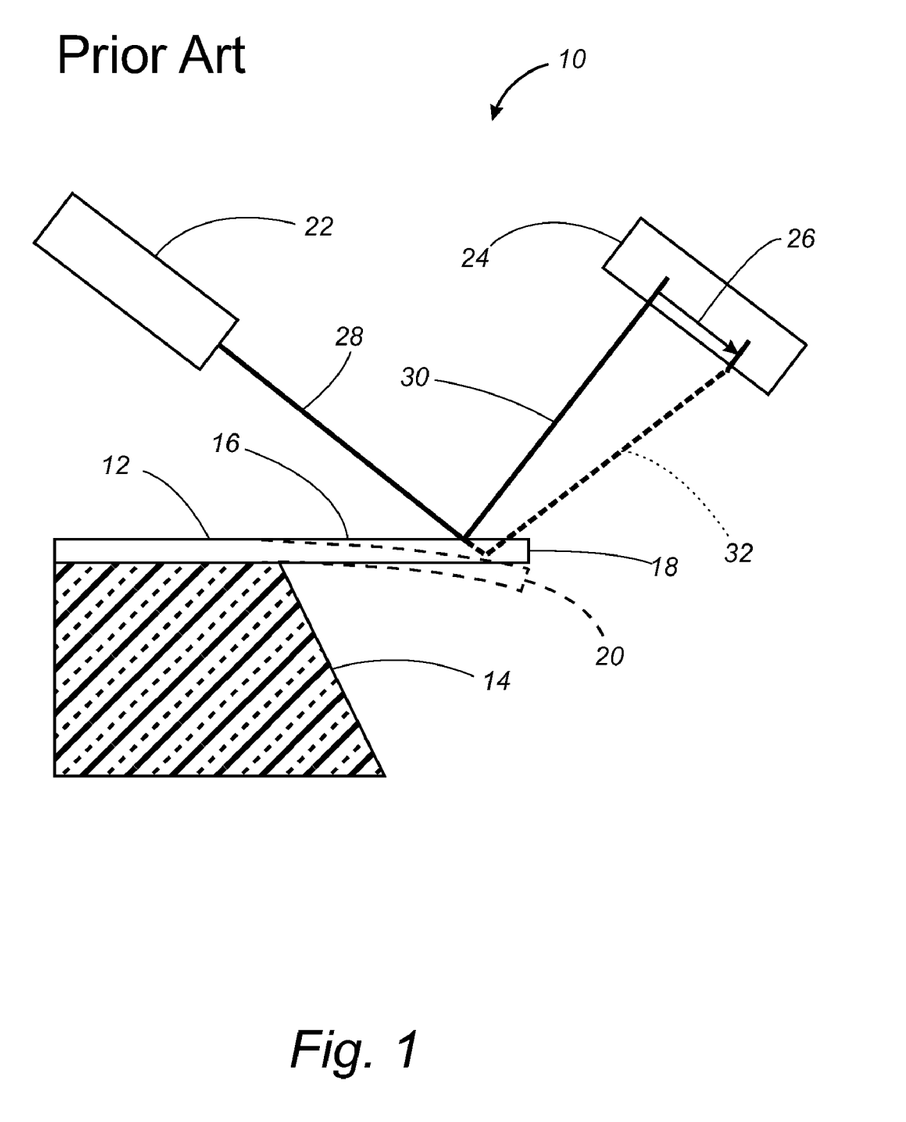
FIG. 1 is a schematic of a prior art cantilever based sensor using an optical sensing technique.

Recently, biosensors utilizing cantilever bending caused by surface stress change has attracted special attention. FIG. 1 provides a schematic demonstrating the operating principle of such cantilevers. Cantilever sensing system 10 includes micro-cantilever 12 mounted on substrate 14. Micro-cantilever 12 is immobilized with a probe layer of bio-specific molecules (e.g., probe single-stranded DNA) on side 16. The selective binding of target bio-molecules (e.g., complementary single-stranded DNA) to immobilized probe layer results in a surface stress change that causes a mechanical bending of the cantilever from position 18 to position 20 or vice versa. Accordingly, the existence of target biomolecules can be detected by monitoring the bending of the cantilever. Typically, the bending is monitored with an optical lever technique that includes laser 22 and photosensor 24. The bending of microcantilever 12 is detected as movement along direction 26 of laser beam 28 from along laser beam path 30 to path 32. The unique advantage of this prior art sensing scheme is that it is a label-free assay in that there is no need to label the target biomolecules with fluorescent dyes or radioisotopes.

The displacement of the cantilever tip can be described by the following equation:

$$\Delta z = \frac{3(1-v)L^2}{EH^2}\Delta\sigma$$

where v is Poisson's ratio, E is Young's modulus, H is the cantilever thickness, L is the cantilever length and $\Delta\sigma$ is the surface stress change generated by the adsorbed molecules. The surface stress generated by molecule recognition is usually very small. For instance, the DNA hybridization results in a surface stress change in the order of $10^{-3}$ N/m. So far, the majority of cantilever biosensors are fabricated using LPCVD (low pressure chemical vapor deposition) silicon nitride, with a Young's modulus between 260 GPa and 330 GPa, or silicon, with a Young's modulus of ~160 GPa. For a typical nitride cantilever, 250 µm long, 200 µm wide, and 0.5 µm thick, the deflection of the cantilever tip caused by a $1\times10^{-3}$ N/m surface stress is only ~2 nm. The extremely low value for the deflection is the reason why the optical lever method is almost exclusively used to detect the cantilever bending as shown in FIG. 1.

The detection of DNA hybridization, DNA single-nucleotide mismatches, prostate-specific antigen (PSA), two cardiac biomarker proteins (creatin kinase and myoglobin), and glucose have been demonstrated using the optical cantilever method. Moreover, microcantilever based sensors have proven to be a very promising platform for a wide variety of biosensing applications. The cantilever sensor technique can be a universal platform for the detection of various specific biomolecular bindings such as DNA hybridization, DNA-RNA binding, antigen-antibody binding, protein-ligand binding, and DNA-protein binding since the cantilever motion is driven by free-energy change, which is universal for almost all specific biomolecular bindings.

Currently, the optical lever method is almost exclusively used to detect the nanoscale deflection of cantilevers in the literatures. Although the optical method offers excellent sensitivity, it has several intrinsic disadvantages. First, the system can not be miniaturized. Second, the optical system is expensive (a laser source and a photosensor with associated readout circuits can easily exceed $2000). Third, it is difficult to monitor large 2-D cantilever arrays using optical lever method.

Accordingly, it is desirable to provide a cantilever sensor that is inexpensive and capable of being miniaturized.

SUMMARY OF THE INVENTION

The present invention overcomes the problems encountered in the prior art by providing in one embodiment a cantilever sensor comprising a supporting substrate, a cantilever spring element at least partially disposed over the support substrate, a probe layer disposed over the first side of the cantilever spring element, and a piezoresistive transducer attached to the second side of the cantilever spring element. The cantilever spring element is characterized by having a first side and a second side and comprising a polymer having a Young's modulus less than about 100 Gpa,. Sensing systems that incorporate the cantilever sensor of the invention include a detector in communication with the piezoresistive transducer to provide measurements of surface strain changes in the piezoresistive transducer. The cantilever sensors of the invention advantageously allow for a label-free assay. Moreover, the cantilever sensors of the invention are miniaturizable and portable with the bulky optical components of the prior art systems being eliminated. Reduction in the cantilever dimensions allows for high density sensor arrays to be fabricated. Since the output from the piezoresistive transducer is an electrical signal, these signals are easily and inexpensively processed.

In another embodiment of the invention, a method for forming the cantilever sensor of the invention is provided. The method of the invention comprises depositing a polymer layer on a substrate. The deposited polymer layer is then patterned into a shape corresponding to one or more cantilever spring elements. A portion of the substrate is etched to expose one or more cantilever springs. Next, a probe layer is formed on the polymer layer. In certain variations of the method of the invention, a piezoresitive transducer is deposited onto the substrate prior to the deposition of the polymer layer. In a variation of this embodiment, the method of the invention is a low temperature and post-CMOS compatible process.

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

Figure 2A:
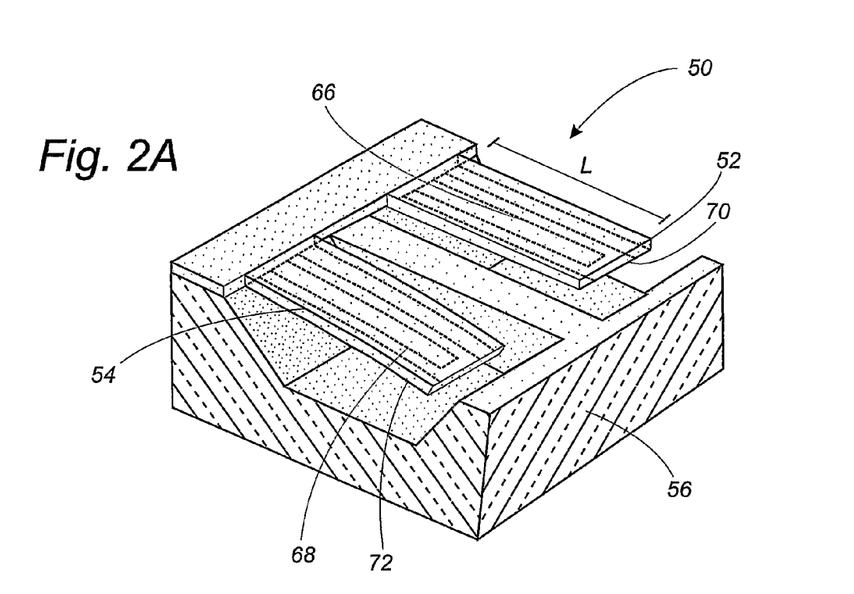
FIG. 2A is a perspective view of an embodiment of the piezoresistive cantilever sensors of the present invention.
Figure 2B:
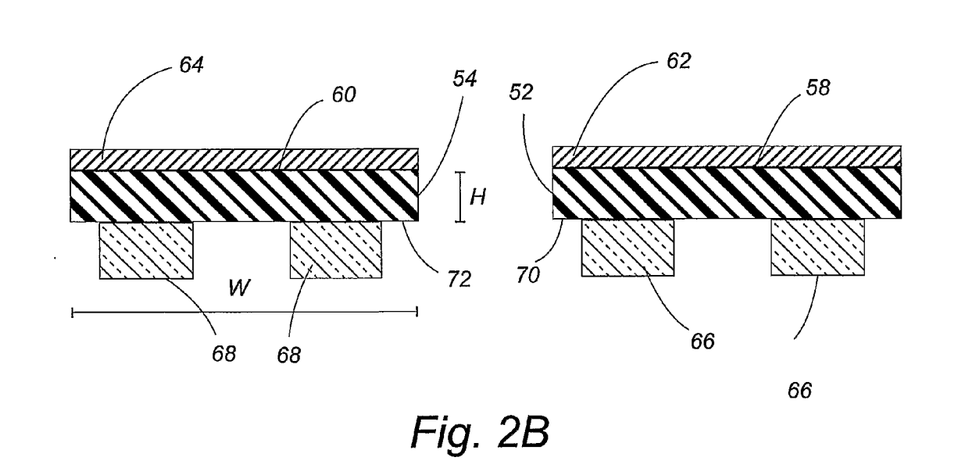
FIG. 2B is a cross-sectional view of a pair of piezoresistive cantilever sensors of the present invention.

With reference to FIGS. 2A and 2B, schematics of the piezoresistive cantilevers of the present invention are provided. Cantilever sensor 50 includes cantilever spring elements 52, 54 attached to supporting substrate 56. In some variations of the invention, supporting substrate 56 is a semiconductor wafer. Disposed over first sides 58, 60 of the cantilever spring elements 52, 54 are probe layers 62, 64. In order to act as sensors these probe layers will incorporate a suitable probe material that comprises a plurality of probe molecules or sites that bind to target molecules. Examples of biomolecular bindings that are used by the probe material include DNA hybridization, DNA-RNA binding, antigen-antibody binding, protein-ligand binding, and DNA-protein binding. Moreover, suitable probe material include materials for detecting DNA hybridization, DNA single-nucleotide mismatches, prostate-specific antigen (PSA), cardiac biomarker proteins, glucose and the like. For example, probe layers 62, 64 may be immobilized with pre-synthesized ssDNA probes that are complementary to a desired target nucleotide sequence. To facilitate the immobilization of probe molecules, a thin gold layer is usually first deposited on the cantilever surfaces. Cantilever spring elements 52, 54 are each characterized by length L, width W, and thickness H. Cantilever spring elements 52, 54 will typically have a surface area from about $1 \times 10^2$ μm² to about $1 \times 10^6$ μm² and a thickness of about 0.1 to about 20 μm. Piezoresistive transducers 66, 68 are attached to second sides 70, 72 (i.e., on the side closest to substrate 56) of the cantilever spring elements 52, 54. Piezoresistive transducers 66, 68 are characterized by dimensions of length, width, and height and by the resistance. Suitable piezoresistive transducers are polysilicon or single crystal silicon piezoresistors. The design parameters for cantilever spring elements 52, 54 and piezorestive transducers 66, 68 are correlated and the selection is mainly based on two criteria: (1) maximize the sensitivity; and (2) minimize the noise. In a fully operational sensor system, a detector is in communication with piezoresistive transducers 66, 68 to provide measurements of the surface strain changes in piezoresistive transducers 66, 68.

The utilization of piezoresistive sensing by the cantilever sensors of the present invention allows for sensing systems that are inexpensive and that can be miniaturized. The surface strain of the cantilever caused by the bending is $$\varepsilon = \frac{3(1-v)}{EH}\Delta\sigma \tag{2}$$

and that the resistance change of the piezoresistor is $$\frac{\Delta R}{R} = \varepsilon G \tag{3}$$

where G is the gauge factor of the piezoresistor. For boron-doped polysilicon piezoresistors (doping concentration $10^{19}$/cm³), G is approximately 30. If a $1 \times 10^{-3}$ N/m surface stress is applied on a 250 μm×200 μm×0.5 μm nitride cantilever, the corresponding strain and relative resistance change of polysilicon piezoresistor will be $1.6 \times 10^{-3}$ and $4.8 \times 10^{-7}$, respectively. Such a level of strain/resistance change is difficult to detect.

From equations (1) and (2), it is observed that the displacement of the cantilever tip and surface strain are both inversely proportional to the Young's modulus of the cantilever material. Therefore, since cantilever spring elements 52, 54 are made from a softer material the sensitivity is much higher. Suitable materials for the fabrication of cantilever spring elements 52, 54 are polymers having a Young's modulus less than about 100 GPa. In another variation of the invention, cantilever spring elements 52, 54 comprise polymers having a Young's modulus less than about 50 GPa. In yet another variation of the invention, cantilever spring elements 52, 54 comprise polymers having a Young's modulus less than about 10 GPa. In yet another variation of the invention, cantilever spring elements 52, 54 comprise polymers having a Young's modulus less than about 5 GPa. In some variations, useful polymers are sublimable at relatively low temperatures (at 100° C. or below). Such sublimable thermoplastic polymers are capable of being deposited by vapor phase deposition at temperatures of about 100° C. or less. Particularly useful polymers include thermoplastic polymers such as Parylene. Parylene is the generic name for members of a unique family of thermoplastic polymers. Parylene deposition is a room temperature, highly conformal, vapor phase process. Parylene is chemically inert and is not etched by TMAH or KOH. There are three types of parylenes commonly used: parylene N, C and D. Combinations of these Parylenes may also be used in the practice of the invention. Among the three types, parylene C is especially suitable for our application. Parylene C has a Young's modulus of 2.8 GPa, two orders of magnitude smaller than that of silicon nitride. For a 250 μm long, 200 μm wide, and 2 μm thick parylene C cantilever, the displacement of the tip caused by $1 \times 10^{-3}$ N/m surface stress is 12.6 nm, ~6 times of the nitride cantilever. More importantly, the surface strain is increased from $1.6 \times 10^{-8}$ to $4.0 \times 10^{-7}$, by a factor of 25. By optimizing the design, even larger surface strain can be achieved. If polysilicon piezoresistors are employed, the resulting relative resistance change will be $1.2 \times 10^{-6}$, which can be readily measured. Therefore, it is possible to detect the bending using piezoresistive sensing. This can lead to a cheap and miniaturized biosensing apparatus.

The sensitivity of the cantilever sensor of the invention can be described using equation (2). For the convenience, equation (2) is rewritten here:

$$\varepsilon = \frac{3(1-\nu)}{EH}\Delta\sigma \quad (2)$$

From equation 2, it can be observed that the cantilever thickness should be as small as possible to maximize the surface strain. However, the achievable thickness is limited by the fact that it is difficult to fabricate very thin cantilevers. Moreover, too thin a cantilever is undesirable because such a thin cantilever will be too thin to bend the polysilicon piezoresistor. Accordingly, there is an optimal thickness.

It can also be observed from equation (2) that the surface strain is not a function of the cantilever width and length. This is very beneficial since a short cantilever can be employed to save chip space and less target biomolecules are needed to bend the cantilever. The piezoresistive cantilever sensors can be readily expanded to a high density large-scale 2-D array, enabling high-throughput parallel sensing. However, it should be appreciated that the cantilever can not be too short, since the piezoresistors need to have reasonably large resistance to minimize the joule heat during operation.

There are two concerns of the parylene piezoresistive cantilevers. The first is the joule heat generated when electrical current flows through the piezoresistors, which may cause deflection due to the bimetallic effect. Since the cantilever is operated in liquid and the power applied can be minimized by employing large resistance, the temperature increase will not be significant. In addition, a reference cantilever will be incorporated to cancel this common mode signal. The second concern is the stability of the parylene cantilevers. The common mode drift can be easily cancelled by differential sensing. The non-common mode drift is generally small within a short period of time. It will not be a big issue since the signal is the static deflection change within 15 min~30 min. Long term non-common mode drift will not affect the reading at all.

The minimum detectable signal of the cantilever sensors of the invention is determined by the noise. There are several noise sources for the piezoresistive cantilever. First one is the thermal noise caused by the Brownian motion (thermal motion) of ambient water molecules. The second noise source is the Johnson noise of the piezoresistor, which is caused by the thermal motion of electrons. The third noise source is 1/f noise. Since the cantilever is operated in static mode, 1/f noise will dominate. The noise spectral density at 1 Hz is at the level of $10^{-6}$V/Hz$^{1/2}$ for a 65 μm×20 μm×0.36 μm polysilicon resistor with a resistivity of 0.02 Ωcm. The product of the length, width, and thickness of the piezoresistor needs to be as large as possible to minimize the 1/f noise. However, if the polysilicon piezoresistor is too stiff, the sensitivity will be decreased. It is worth noting that the cantilevers operate in static mode with the measure deflection being the static deflection. Accordingly, the signal bandwidth is very narrow enabling a fairly high signal to noise ratio to be achieved.

In another embodiment of the invention, a method for forming the cantilever sensor of the invention is provided. In a particular variation of this embodiment, the method of the invention comprises depositing a silicon layer onto a substrate. Such a silicon layer may be either a single crystalline layer or a polycrystalline layer. This layer will be used as the piezoresistive layer. This layer is usually doped with a dopant such as boron atoms. Next, the device is overcoated with the polymer layer set forth above. The deposited polymer layer is then patterned into a shape corresponding to one or more cantilever spring elements. A portion of the substrate is then etched to expose one or more cantilever springs. Such etching techniques may be either dry etching or wet etching. Next, a probe layer is formed on the polymer layer. FIGS. 3-6 described below provide specific examples of the implementation of the methods of this embodiment.

Fabrication

Parylene cantilevers with 50 μm×50 μm×2 μm dimensions and a 50 μm×5 μm×0.25 μm polysilicon resistor (the piezoresitor) are modeled. Table 1 compares the performance of a nitride cantilever and two parylene C cantilevers. It can be observed 50 μm long parylene cantilever has the same surface strain as the 250 μm long one. However, the displacement at the tip is much smaller. This clearly shows that piezoresistive sensing allows much smaller cantilevers.

TABLE 1

Cantilever dimensions with displacement and surface strain values

| Cantilevers (L × W × H) | Displacement at the tip by a surface stress of $10^{-3}$ N/m | Surface strain caused by a surface stress of $10^{-3}$ N/m |
|---|---|---|
| Nitride 250 μm × 200 μm × 0.5 μm | 2.0 nm | $1.6 \times 10^{-8}$ |
| Parylene C 250 μm × 200 μm × 2 μm | 12.6 nm | $4.0 \times 10^{-7}$ |
| Parylene C 50 μm × 50 μm × 2 μm | 0.5 nm | $4.0 \times 10^{-7}$ |

Figure 3A:
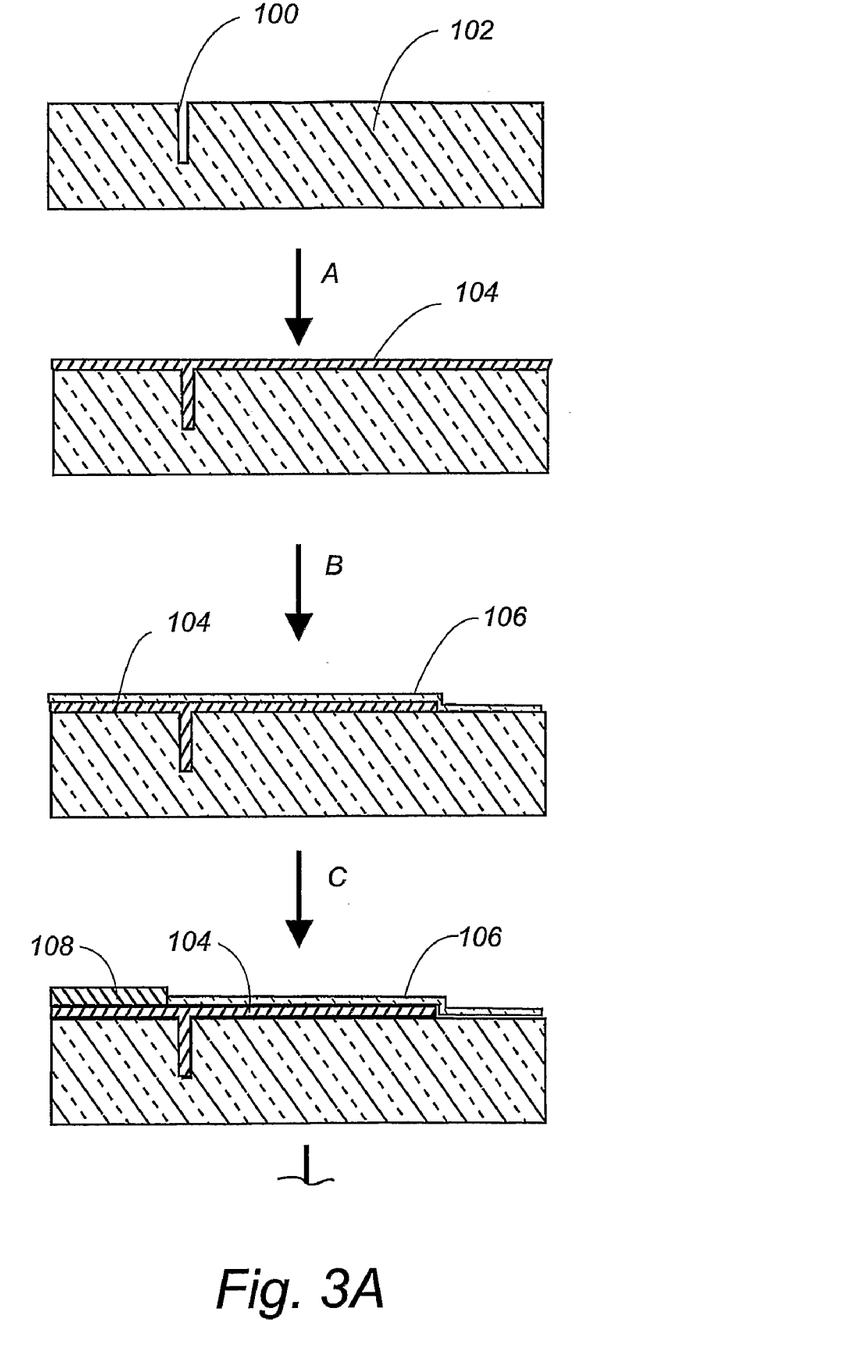
FIGS. 3A-B provide a flow chart illustrating an example of a method for forming the piezoresistive cantilevers of the present invention.
Figure 3B:
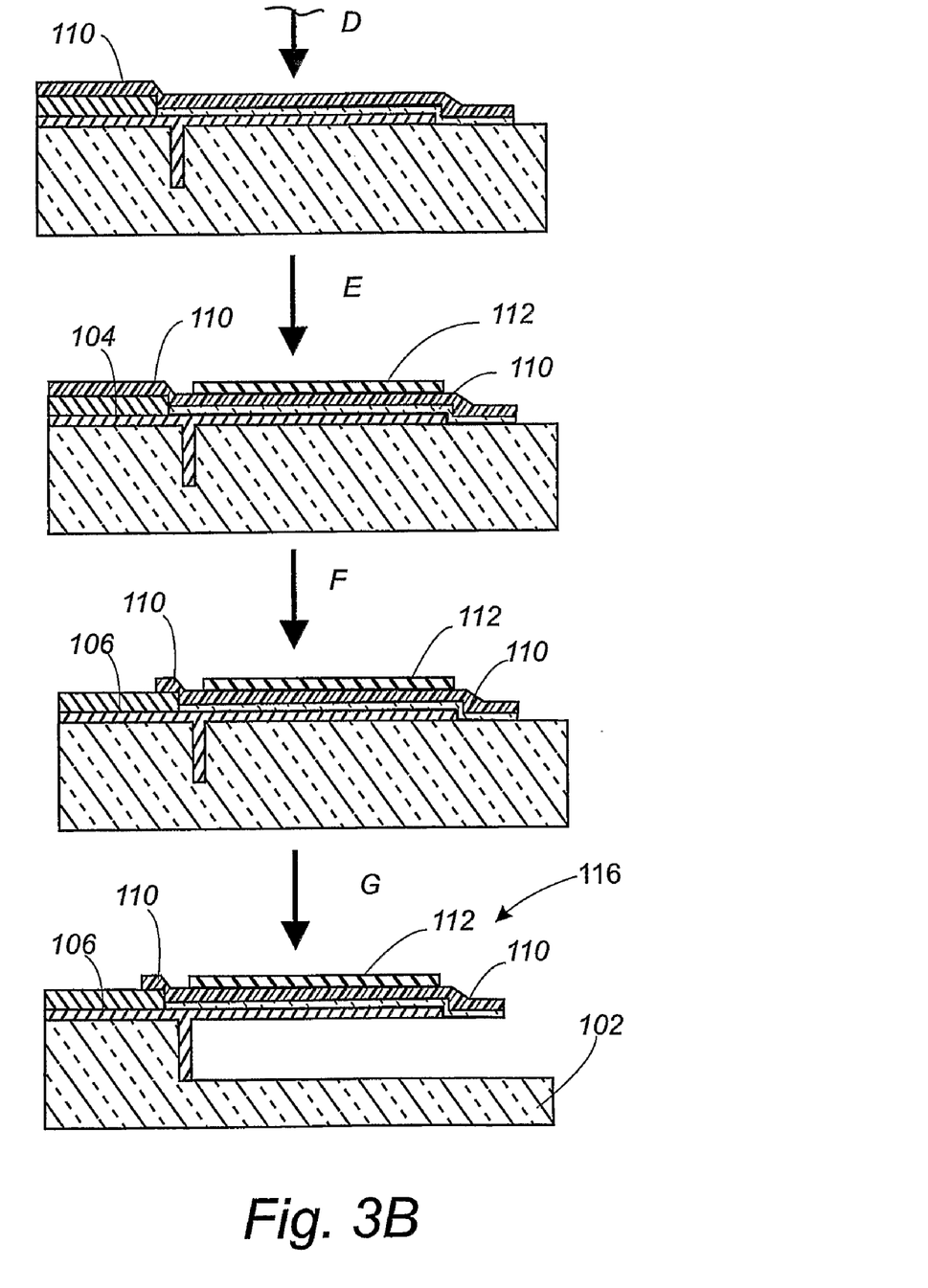

With reference to FIG. 3, a schematic in cross-section illustrating an example of a fabrication method for making the piezoresistive cantilevers of the invention is provided. Trench 100 is etched by Deep Reactive Ion Etching. In step A, an oxide layer (about 50 nm) is grown on substrate 102 followed by the deposition of polysilicon layer 104. In step B, polysilicon layer 104 is doped twice and the polysilicon layer 104 is patterned. The first doping is a global boron ion implantation, resulting in a doping concentration of $2\times10^{19}$/cm$^3$. At this doping concentration, the gauge factor of polysilicon is about 30 and the temperature coefficient of resistance ("TCR") is close to zero. The second doping is a selective high-dose boron ion implantation, resulting in a doping concentration of $2\times10^{20}$/cm$^3$, on the contact areas of the piezoresistors. Finally, in step B, dry oxide layer 106 (about 50 nm) is grown. In step C, contact holes are opened and metal interconnect wires 108 are evaporated and patterned. In step D, polymer layer 110, is deposited and patterned. The exposed silicon dioxide is removed. A useful polymer layer is parylene C at a thickness of about 2 microns. In step E, Au/Cr layer 112 is deposited and patterned. In step F, bonding pads are opened. Finally, in step G a portion of substrate 102 is etched away to reveal cantilever 116. A suitable etch is achieved with XeF$_2$ with etches isotropically. It should be appreciated that the method of the present example embraces variations in which the thicknesses of each layer set forth above for FIG. 3 are varied. Similarly, the processes by which each layer is formed can be substituted by processes for layer deposition and/or doping known to those skilled in the art. It should be noted that in step E, the deposition of Au/Cr layers, can be carried out after the releasing of cantilevers.

Figure 4:
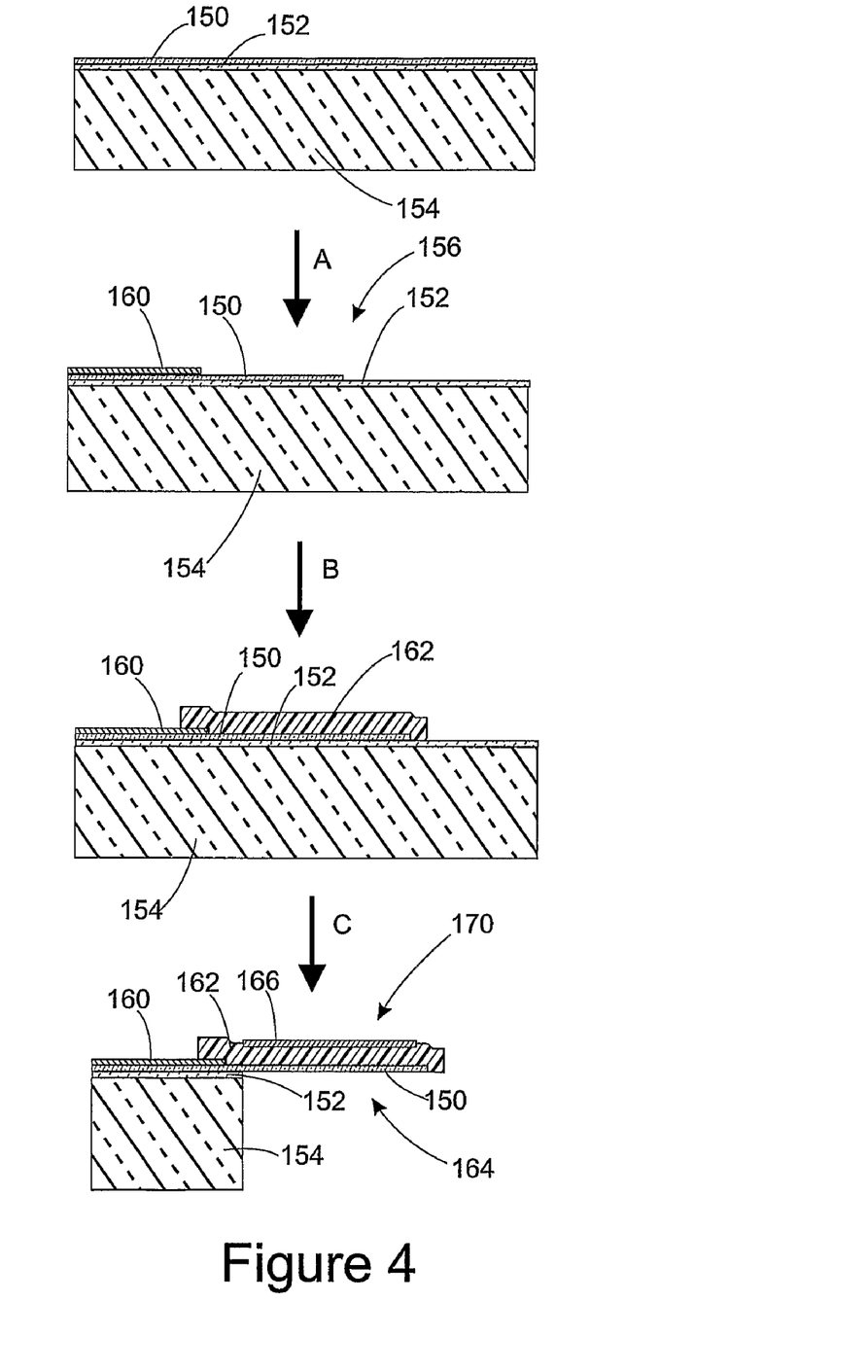
FIG. 4 is flow chart illustrating another example of a method for forming the piezoresistive cantilevers of the present invention.

With reference to FIG. 4 a schematic illustrating another example of a fabrication method for making the piezoresistive cantilevers of the invention is provided. The cantilever of this embodiment is based on a silicon-on-insulator (SOI) wafer with 100 nm device layer. The fabrication process starts with the doping of silicon layer 150 which is disposed over oxide layer 152. Oxide layer 152 is in turn disposed over wafer 154. Although any thickness compatible with the function requirements of the cantilever is possible, a thickness of about 100 nm is suitable. Silicon layer 150 is doped with boron ions twice. The first doping is a global boron ion implantation with a dose of $3 \times 10^{13}/cm^2$ which results in a doping concentration of about $3 \times 10^{18}/cm^3$ and a nearly zero TCR. The second doping is a selective high-dose boron ion implantation with a dose of $2 \times 10^{15}/cm^2$, resulting in a doping concentration of $2 \times 10^{20}/cm^3$, on the contact areas of the piezoresistors. After high temperature annealing to active the dopants, silicon layer 150 is patterned to form the piezoresistor 156 (Step A). Thin oxide on contact holes are then removed using the same mask for high-dose ion implantation. Metal layer 160 (e.g. Al or Au/Cr) is sputtered and patterned to form the interconnect wires. In Step B, parylene C layer 162 (about 2 µm) is deposited with A-174 adhesion promoter and subsequently patterned by oxygen plasma. In Step C, the wafer is then etched from backside using DRIE to release cantilever section 164. The oxide layer, which serves as the etch stop during DRIE etching, is removed by HF next. Finally, 20 nm gold and 5 nm Cr layers 166 are evaporated on the top surface of the cantilever using a shadow mask to complete cantilever 170. Although the piezoresistors of FIG. 4 are formed by single crystalline silicon, polysilicon can also be employed without changing the fabrication process significantly. Moreover, the method of the present example embraces variations in which the thicknesses of each layer set forth above for FIG. 4 are varied. Similarly, the processes by which each layer is formed can be substituted by processes for layer deposition and/or doping known to those skilled in the art.

Figure 5:
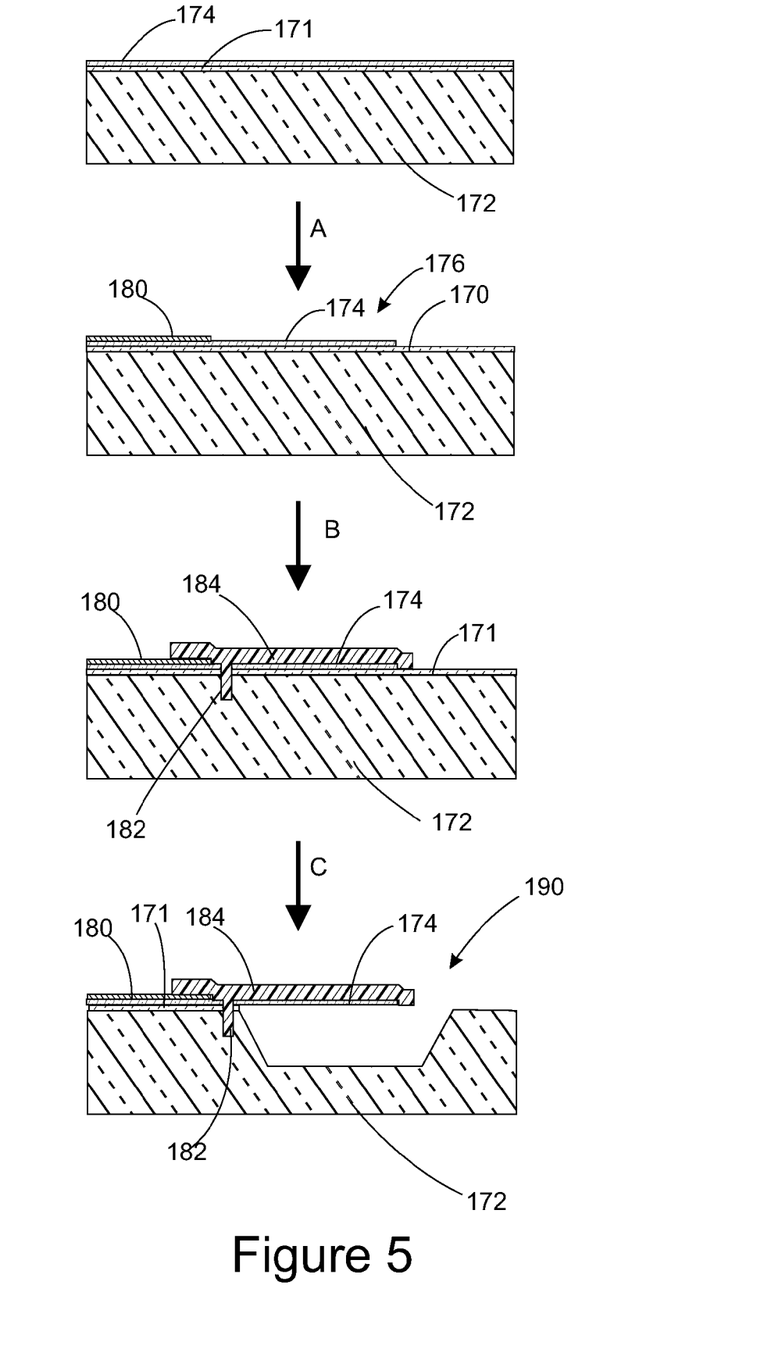
FIG. 5 is flow chart illustrating yet another example of a method for forming the piezoelectric cantilevers of the present invention.

With reference to FIG. 5 a schematic illustrating an example of yet another fabrication method for making the piezoresistive cantilevers of the invention using wet etches is provided. Wet anisotropic silicon etchant such as TMAH are found to be useful for making the cantilevers of the invention. At certain pH values, TMAH does not etch aluminum and is CMOS-compatible. FIG. 5 illustrates a process based on TMAH etching in which polysilicon piezoresistors are used. Single crystalline silicon can also be employed in the method of FIG. 5. It has been observed that TMAH does not significantly etch parylene C. However, TMAH does attack interfaces with parylene C causing parylene films to peel off. Accordingly, anchoring holes are used in the present example to prevent peeling off during TMAH etching.

The process of FIG. 5 starts with the thermal growth of oxide layer 171 (e.g. about 50 nm) on silicon wafer 172 (e.g. a (100) silicon wafer). Next, polysilicon layer174 (e.g. about 100 nm thick) is deposited, and subsequently doped, annealed (e.g. 1050° C.), and patterned to form piezoresistor 176. In a similar manner to the doping of silicon wafers, polysilicon layer 174 is doped twice. The first doping is a global boron ion implantation with a dose of $2 \times 10^{14}/cm^2$, resulting in a doping concentration of $2 \times 10^{19}/cm^3$. This leads to a nearly zero TCR. The second doping is a selective high-dose boron ion implantation on the contact areas of the piezoresistors for ohmic contact. In Step A, an oxide layer(e.g. about 20 nm) is grown over polysilicon layer 174 using dry oxidation. This oxide layer is used to protect polysilicon layer 174 from TMAH etching. Contact holes are then opened using the same mask used for the high-dose ion implantation. Next metal layer 180 is applied. In Step B, after etching anchoring holes 182, parylene C layer 184 is deposited and patterned. Exposed silicon dioxide is removed. In Step C, the wafer is immersed in TMAH solution and cantilever 190 is formed by undercutting silicon. If the undercut rate is 0.5 µm/min, it takes 50 minutes to free the 25 µm long cantilevers. An oxide etch rate in TMAH of approximately 0.2 nm/min is observed ensuring that a 20 nm oxide thickness is sufficient. Diluted TMAH (e.g., 5%) is found to be more useful than undiluted TMAH since diluted TMAH exhibits a higher etch rate. The etched surface of silicon by diluted TMAH is very rough and reduces stiction. The oxide etch rate might also be smaller. Finally, thin Au/Cr layers are evaporated using a shadow mask to complete the fabrication of cantilever 190. The method of the present example embraces variations in which the thicknesses of each layer set forth above for FIG. 5 are varied. Similarly, the processes by which each layer are formed can be substituted by processes for layer deposition and/or doping known to those skilled in the art.

The TMAH etching is more advantageous than DRIE for the following reasons. First, the TMAH process is cheaper and simpler. Second, the cavity etched by TMAH is well defined by the front side mask and thus has better control of the boundary of the cantilevers. No matter what method is used, DRIE, TMAH, or XeF2, the fabrication process is post-CMOS compatible. Circuits such as multiplexers and amplifiers can be fabricated by CMOS foundry. Then, post-CMOS process can be performed on the wafers. Piezoresistors can be fabricated using the polysilicon layer of CMOS process. SOI CMOS foundry is also available now. Therefore single crystalline silicon piezoresistors can be fabricated using the silicon device layer on SOI wafer. This post-CMOS compatibility would ideally lend the parylene piezoresistive cantilevers to volume manufacturing and low unit cost.

Figure 6:
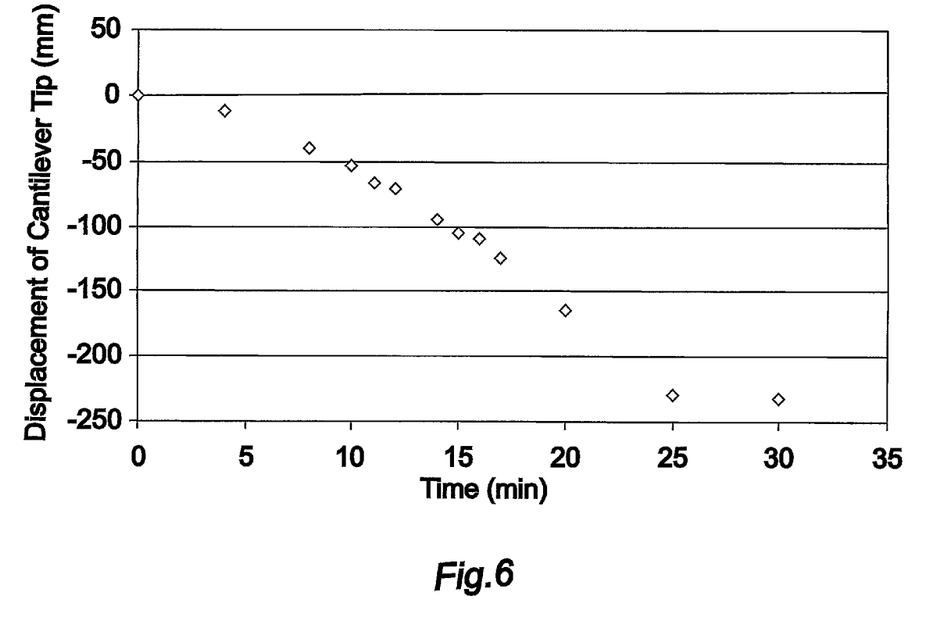
FIG. 6 is a plot showing the response of the cantilever when its top surface is inmobilized with 40-nt-long ssDNA (probe)
Figure 7:
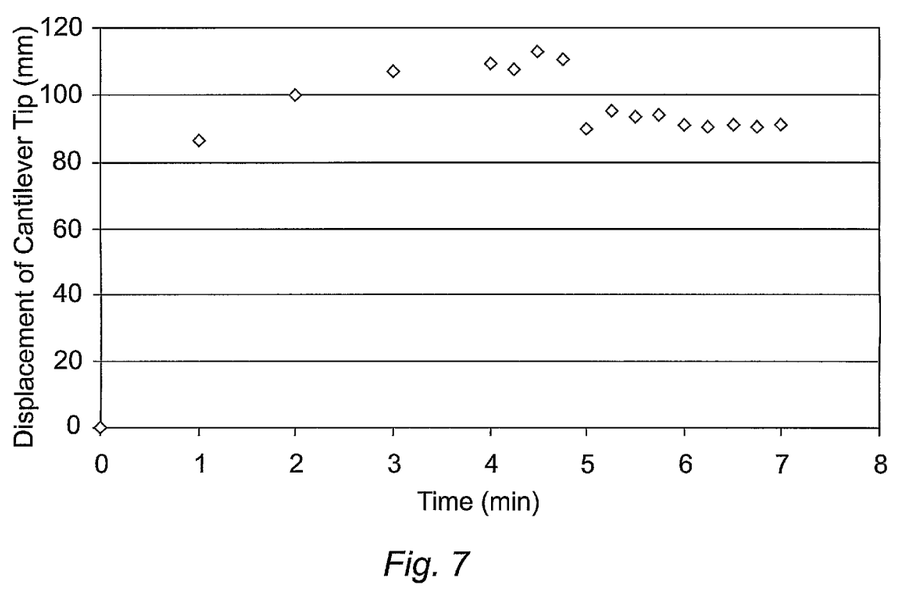
FIG. 7 is a plot showing the response of the cantilever when it is exposed to complimentary target ssDNA.

With reference to FIGS. 6 and 7, the response of a parylene cantilever during the immobilization of probe ssDNA and hybridization of complementary target ssDNA with the probe ssDNA is provided. The trend of the cantilever (bend up or down) during immobilization and hybridization are consistent with other types of cantilevers. However, the magnitude of the cantilever tip displacement is 6~8 times greater than the typically used nitride cantilevers.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A cantilever sensor comprising:
   a supporting substrate;
   a cantilever spring element having a first side and a second side, the cantilever spring element comprising a thermoplastic polymer that is capable of being deposited by vapor phase deposition at a temperature less than 100° C., the thermoplastic polymer having a Young's modulus less than about 100 Gpa, wherein the cantilever spring element is partially disposed over the supporting substrate;
   a probe layer disposed over the first side of the cantilever spring element;
   a piezoresistive transducer attached to the second side of the cantilever spring element; and
   a detector in communication with the piezoresistive transducer, the detector providing measurements of surface strain changes in the piezoresistive transducer.

2. The cantilever sensor of claim 1 wherein the thermoplastic polymer is sublimable at temperatures less than 100° C.

3. The cantilever sensor of claim 1 wherein the thermoplastic polymer is selected from the group consisting of Parylene N, Parylene C, Parylene D, and combinations thereof.

4. The cantilever sensor of claim 1 wherein the probe layer comprises a plurality of probe molecules that bind to target molecules.

5. The cantilever sensor of claim 1 wherein the supporting substrate is a semiconductor wafer.

6. The cantilever sensor of claim 1 wherein the cantilever spring element has an area from about $1\times10^2$ mm$^2$ to about $1\times10^6$ mm$^2$ and a thickness of about 0.1 to about 20 mm.

7. A cantilever sensor comprising:
   a supporting substrate;
   a cantilever spring element having a first side and a second side, the cantilever spring element comprising a thermoplastic polymer, the thermoplastic polymer comprising a parylene, wherein the cantilever spring element is partially disposed over the supporting substrate;
   a probe layer disposed over the first side of the cantilever spring element;
   a piezoresistive transducer attached to the second side of the cantilever spring element; and
   a detector in communication with the piezoresistive transducer, the detector providing measurements of surface strain changes in the piezoresistive transducer.

8. The cantilever sensor of claim 7 wherein the probe layer comprises a plurality of probe molecules that bind to target molecules.

9. The cantilever sensor of claim 7 wherein the thermoplastic polymer is selected from the group consisting of Parylene N, Parylene C, Parylene D, and combinations thereof.

10. The cantilever sensor of claim 7 wherein the support substrate is a semiconductor wafer.

11. The cantilever sensor of claim 7 wherein the cantilever spring element has an area from about $1\times10^2$ mm$^2$ to about $1\times10^6$ mm$^2$ and a thickness of about 0.1 to about 20 mm.

12. A method of forming a cantilever sensor, the method comprising:
    a) depositing a polymer layer on a substrate, the polymer layer comprising a parylene thermoplastic polymer;
    b) patterning the polymer layer into a shape corresponding to one or more cantilever spring elements;
    c) etching a portion of the substrate to expose one or more cantilever springs;
    d) forming a probe layer on the polymer layer; and
    e) attaching a piezoresistive transducer to the polymer layer.

13. The method of claim 12 further comprising etching a trench for anchoring the polymer layer and forming an oxide layer over the substrate prior to step a).

14. The method of claim 13 further comprising depositing a polysilicon layer over the substrate.

15. The method of claim 14 further comprising depositing and patterning metal interconnect wires prior to step a).

16. The method of claim 12 further comprising attaching a piezoresistive transducer to the polymer layer.

17. The method of claim 12 wherein the thermoplastic polymer is selected from the group consisting of Parylene N, Parylene C, Parylene D, and combinations thereof.

18. The method of claim 12 wherein the polymer layer is deposited by vapor phase deposition.

19. The method of claim 12 wherein the probe layer comprises a plurality of probe molecules that bind to target molecules.

20. The method of claim 12 wherein the thermoplastic polymer is a parylene.

* * * * *